(12) United States Patent
Cisel et al.

(10) Patent No.: US 9,492,231 B2
(45) Date of Patent: Nov. 15, 2016

(54) LASER SURGERY DEVICE AND METHOD

(75) Inventors: Brian Cisel, St. Charles, MO (US); Harley Michael Willey, Garland, TX (US); Arash Tom Salamat, Plano, TX (US); Arnold Ochoa, Garland, TX (US); Robert Alan Hasty, Carrollton, TX (US); Mike Wilkinson, Richardson, TX (US)

(73) Assignee: Brian Cisell, St. Charles, MO (US)

( * ) Notice: Subject to any disclaimer, the term of this patent is extended or adjusted under 35 U.S.C. 154(b) by 301 days.

(21) Appl. No.: 13/384,133

(22) PCT Filed: Jul. 9, 2010

(86) PCT No.: PCT/US2010/041506
§ 371 (c)(1),
(2), (4) Date: Feb. 10, 2012

(87) PCT Pub. No.: WO2011/008646
PCT Pub. Date: Jan. 20, 2011

(65) Prior Publication Data
US 2012/0130358 A1    May 24, 2012

Related U.S. Application Data

(60) Provisional application No. 61/225,339, filed on Jul. 14, 2009.

(51) Int. Cl.
*A61B 18/18* (2006.01)
*A61N 5/06* (2006.01)
(Continued)

(52) U.S. Cl.
CPC ............ *A61B 18/22* (2013.01); *A61B 18/20* (2013.01); *A61B 18/203* (2013.01); *A61B 2018/00452* (2013.01); *A61B 2018/1861* (2013.01);
(Continued)

(58) Field of Classification Search
CPC ............ A61B 18/203; A61B 2018/00452; A61B 18/20; A61N 5/062; A61N 2005/0652; A61N 5/0601
USPC ......................... 606/2, 10; 607/88
See application file for complete search history.

(56) References Cited

U.S. PATENT DOCUMENTS

| 4,874,371 A | 10/1989 | Comben |
| 4,895,145 A * | 1/1990 | Joffe ............ A61B 18/20 606/11 |

(Continued)

FOREIGN PATENT DOCUMENTS

| EP | 1118311 A2 | 7/2001 |
| EP | 1021737 B1 | 6/2008 |
| WO | WO93/04727 A1 | 3/1993 |

OTHER PUBLICATIONS

International Search Report and Written Opinion for PCT/US2010/041506 dated Sep. 7, 2010 (16 pages).

*Primary Examiner* — Lynsey Crandall
*Assistant Examiner* — Sebastian X Lukjan
(74) *Attorney, Agent, or Firm* — Polsinelli PC

(57) ABSTRACT

Laser surgery devices and methods of performing laser surgery using laser surgery devices are described. The laser surgery device may rotate a laser fiber along a longitudinal axis of the laser fiber in a repeating pattern through a user-specified rotational pattern. The laser surgery device may be optionally attached to a surgical device to implement hands-free operation of the laser surgery device.

15 Claims, 9 Drawing Sheets

(51) Int. Cl.
  *A61B 18/22* (2006.01)
  *A61B 18/00* (2006.01)
  *A61B 18/20* (2006.01)
(52) U.S. Cl.
  CPC .............. *A61N5/0601* (2013.01); *A61N 5/062* (2013.01); *A61N 2005/0652* (2013.01)

(56) References Cited

U.S. PATENT DOCUMENTS

| | | | |
|---|---|---|---|
| 5,207,672 A | 5/1993 | Roth et al. | |
| 5,269,779 A | 12/1993 | Sogawa et al. | |
| 5,409,483 A * | 4/1995 | Campbell ............ A61N 5/0601 606/13 | |
| 5,454,807 A | 10/1995 | Lennox | |
| 5,586,968 A | 12/1996 | Grundl et al. | |
| 5,733,277 A | 3/1998 | Pallarito | |
| 5,782,848 A | 7/1998 | Lennox | |
| 5,807,383 A | 9/1998 | Kolesa et al. | |
| 5,860,968 A | 1/1999 | Wojcik et al. | |
| 5,949,929 A | 9/1999 | Hamm | |
| 6,126,651 A | 10/2000 | Mayer | |
| 6,152,919 A | 11/2000 | Hakky | |
| 6,562,029 B2 | 5/2003 | Maki | |
| 6,589,233 B1 | 7/2003 | Maki | |
| 6,599,287 B2 | 7/2003 | Iwahashi et al. | |
| 6,602,245 B1 | 8/2003 | Thiberg | |
| 6,621,184 B1 | 9/2003 | Smoliar et al. | |
| 6,764,485 B2 | 7/2004 | Hareyama et al. | |
| 6,986,764 B2 | 1/2006 | Davenport et al. | |
| 7,382,949 B2 | 6/2008 | Bouma et al. | |
| 2001/0029363 A1* | 10/2001 | Lin ................................ 606/5 |
| 2005/0203593 A1* | 9/2005 | Shanks et al. ............... 607/89 |
| 2006/0095099 A1* | 5/2006 | Shanks et al. ............... 607/89 |
| 2006/0200040 A1 | 9/2006 | Weikel, Jr. et al. | |
| 2006/0271131 A1* | 11/2006 | Passy et al. .................. 607/88 |
| 2007/0232902 A1* | 10/2007 | Teramura ..................... 600/425 |
| 2009/0069872 A1* | 3/2009 | Fortuna et al. ................ 607/89 |
| 2009/0088822 A1 | 4/2009 | Pruitt et al. | |

* cited by examiner

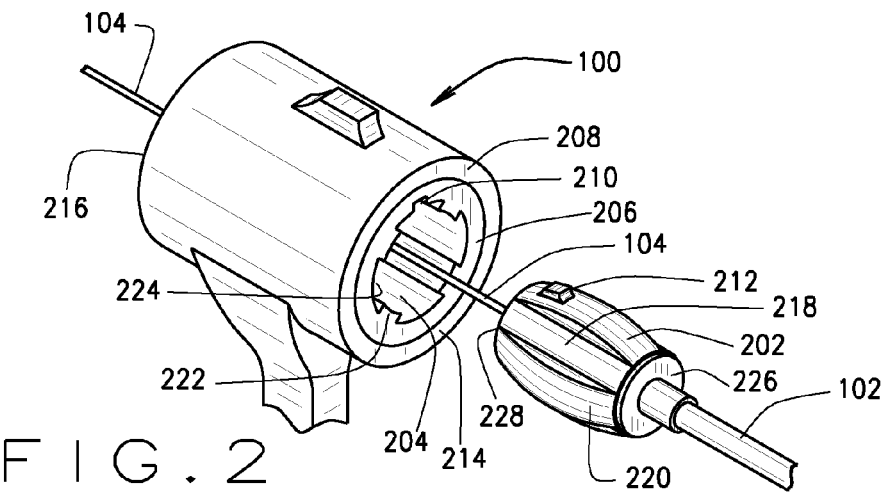
F I G. 2
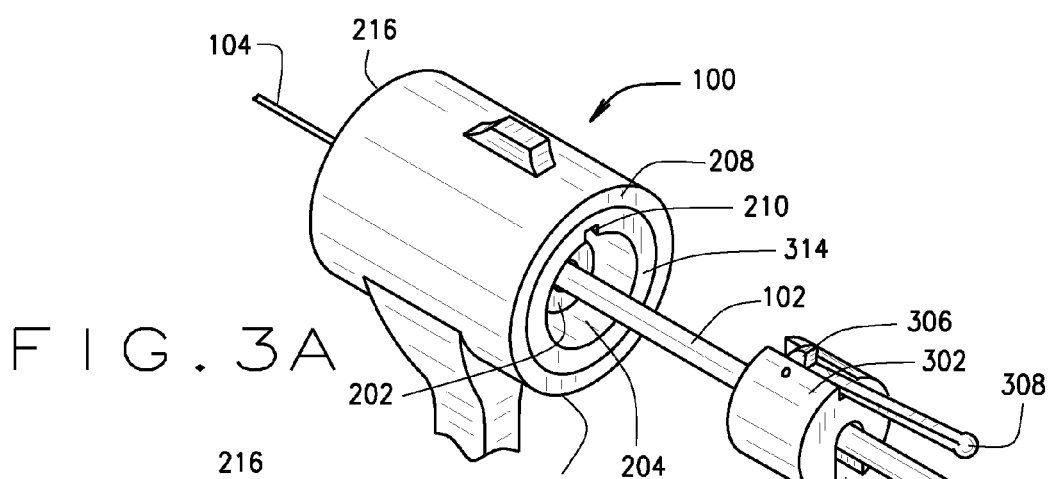
F I G. 3A
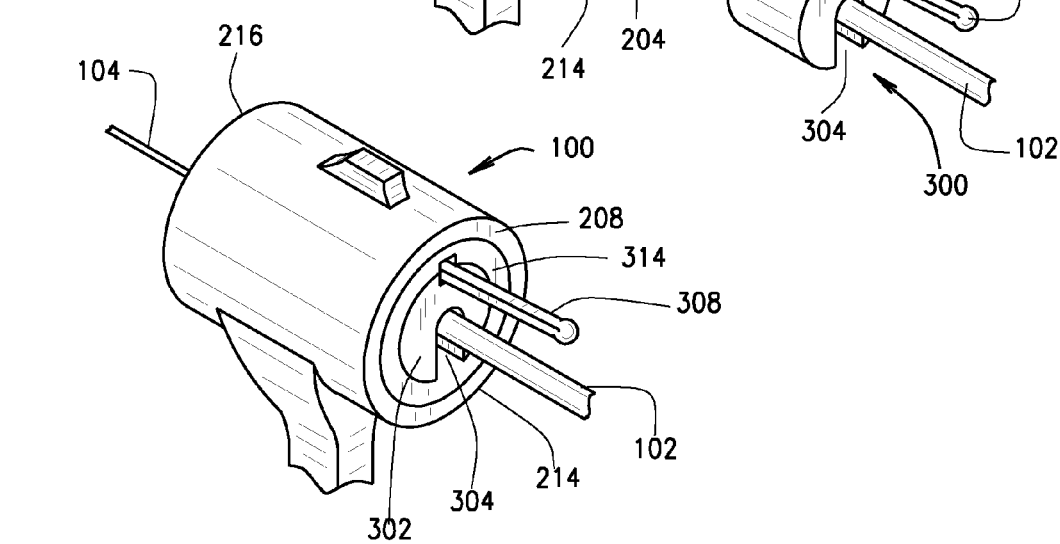
F I G. 3B

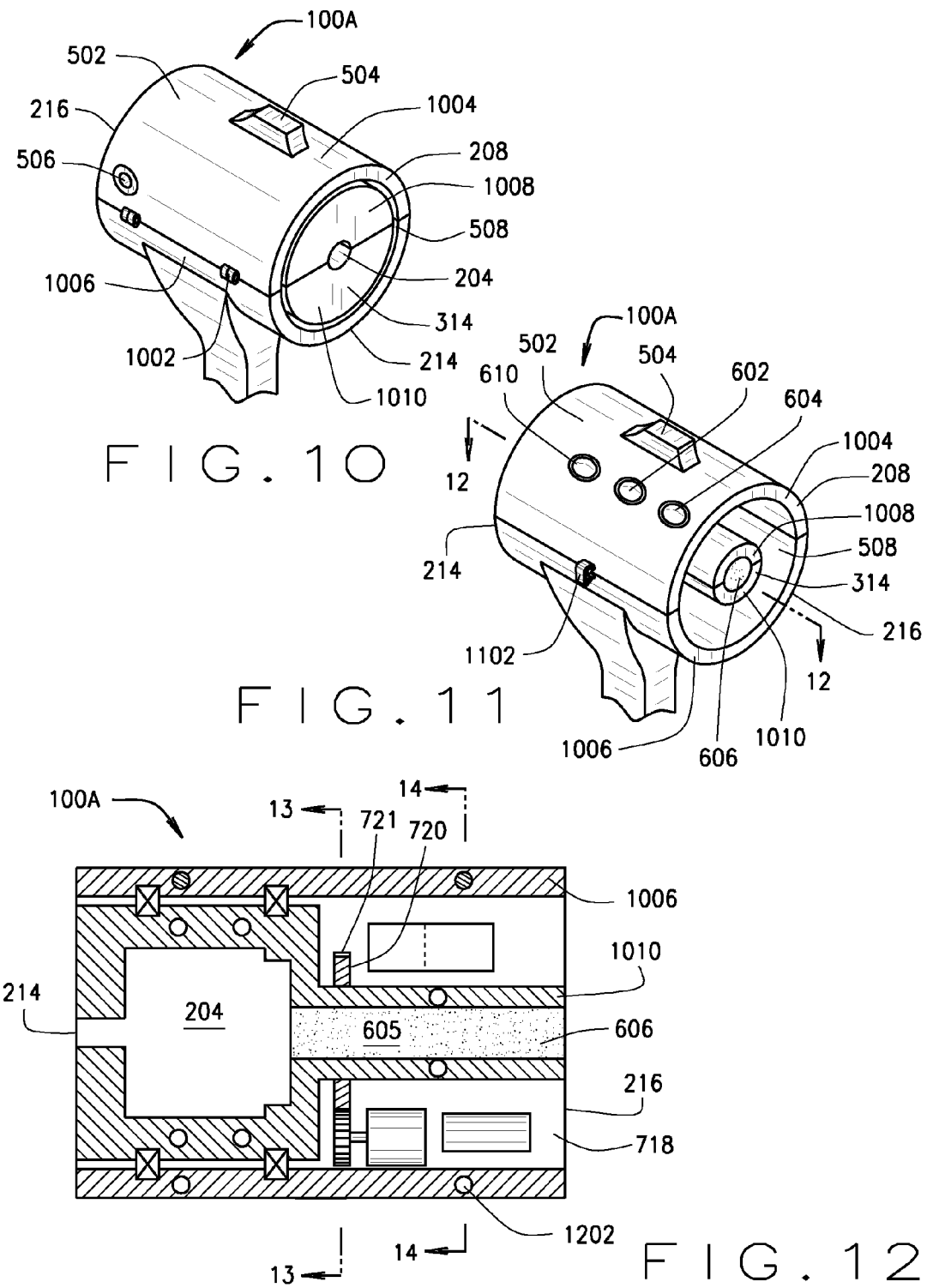

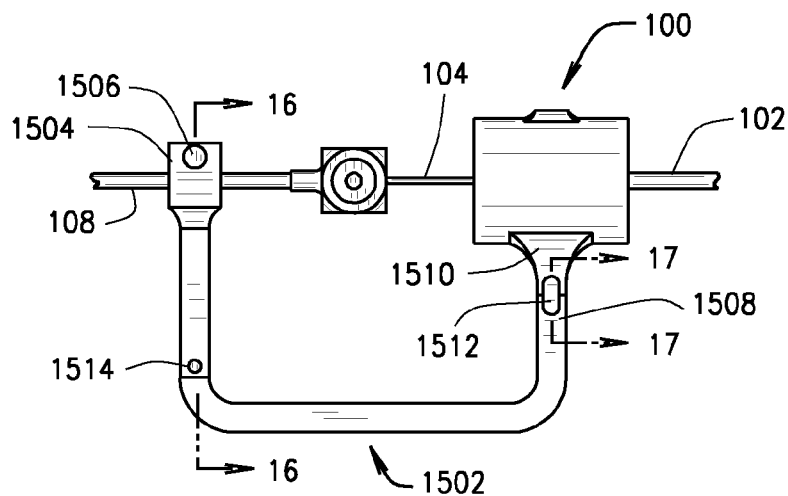
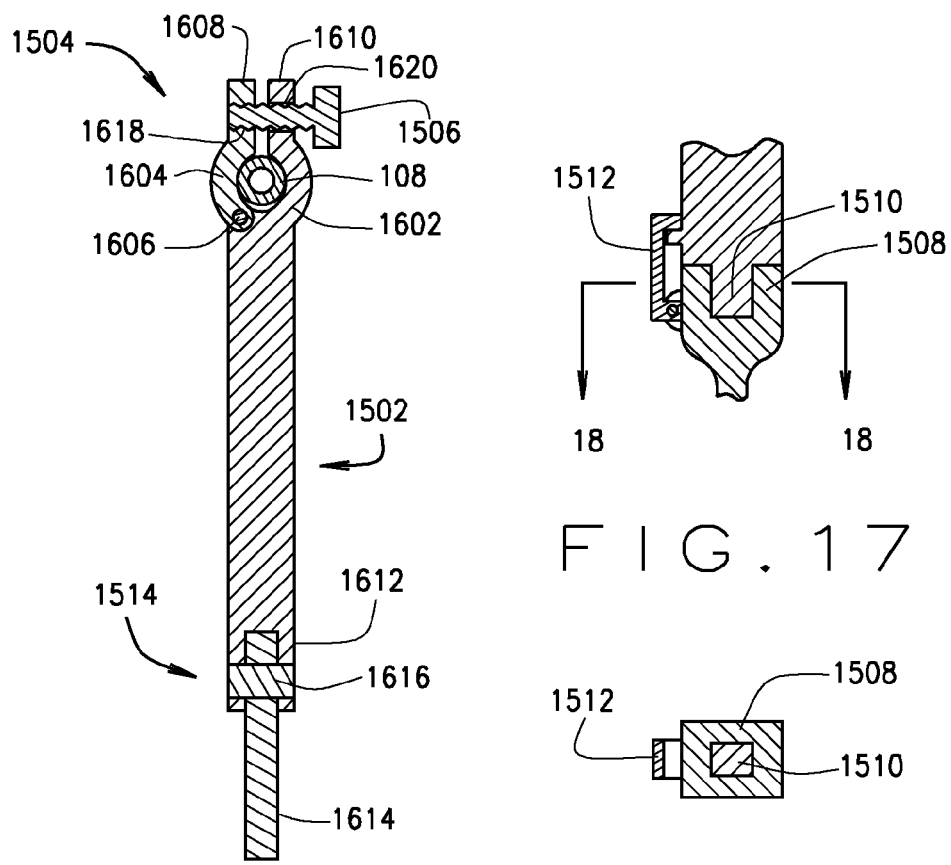
FIG. 15
FIG. 16
FIG. 17
FIG. 18

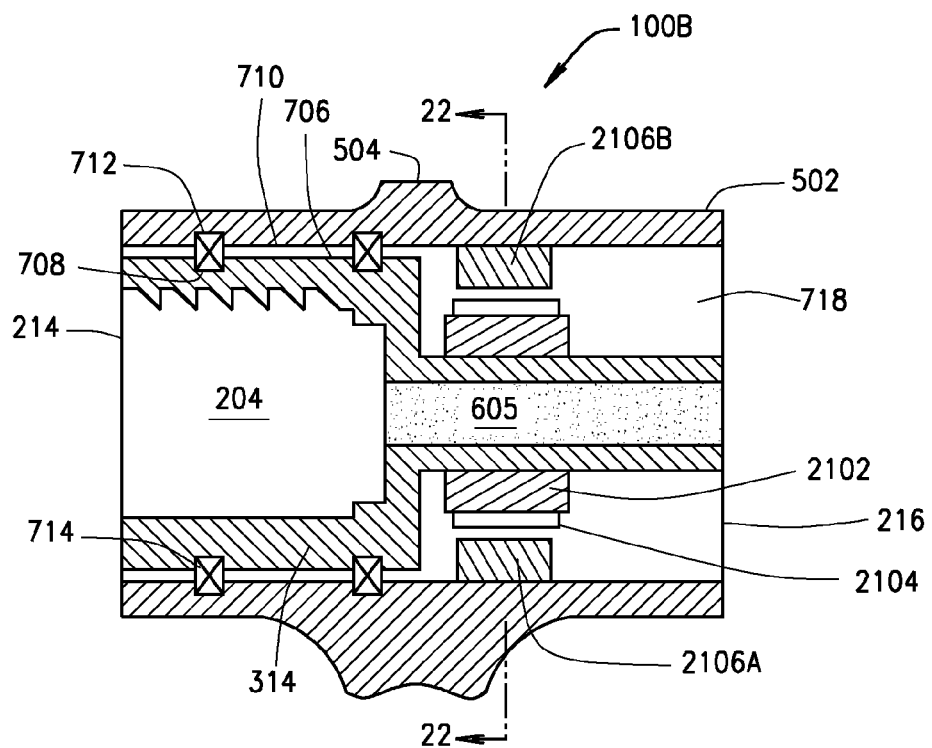
F I G . 2 1
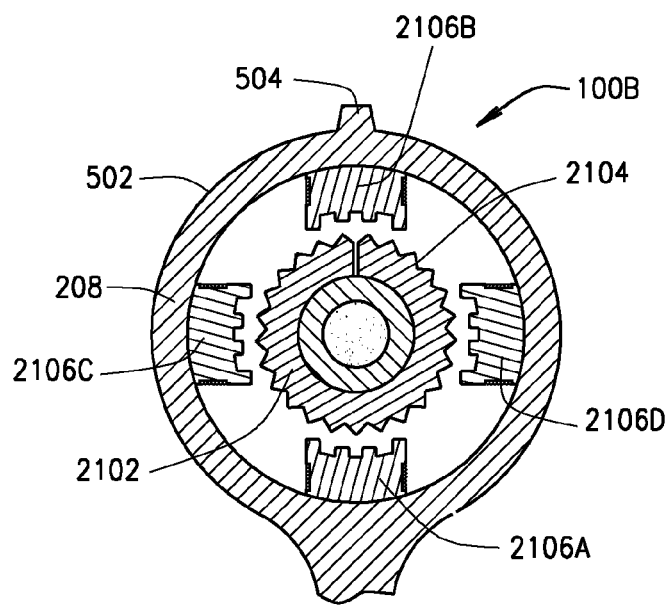
F I G . 2 2

LASER SURGERY DEVICE AND METHOD

FIELD OF THE INVENTION

The present invention relates to laser surgery devices and methods of performing laser surgery using laser surgery devices. In particular, the present invention relates to laser surgery devices to rotate surgical laser fibers about the longitudinal axis of the laser fibers.

BACKGROUND OF THE INVENTION

Surgical lasers are used with increasing frequency for the treatment of benign prostatic hypertrophy (BPH). In recent years, surgical procedures utilizing lasers are gaining status as a preferred surgical procedure for the long-term relief of BPH from the perspective of both urologists and patients. Laser prostate procedures have been touted as the first procedure ever to achieve comparable durability to transurethral resection of the prostate (TURP), the accepted standard of care in this field, and with a lower incidence of complications compared with TURP. However, a significant percentage of physicians prefer more traditional surgical procedures over laser procedure treatments due to negative patient outcomes, prolonged procedure times, and general dissatisfaction with the procedure.

Much of the dissatisfaction with the laser procedure stems from the complexity of the surgical techniques used, as well as the multitude of tasks that must be performed simultaneously by the physician while performing the laser procedure. During this procedure, the physician must execute numerous movements simultaneously, including depressing a foot-pedal to activate the laser with one foot, manipulating the cystoscope with one hand to position a distal tip of the laser fiber to within a few millimeters of target tissue, and rotating a control knob with the other hand to sweep the laser fiber back and forth at a constant speed as well as to insert or retract the distal tip of the laser fiber and/or cystoscope assembly within the surgical site. In addition, the urologist must also monitor numerous other factors such as the patient's vital signs, the video display of the distal tip of the laser fiber in the surgical site, the adjustment of the inflow and the outflow of the irrigation fluid to/from the surgical site, and the laser power commanded from the laser source. As a result, laser procedures are accompanied by a steep learning curve for some urologists in which the initial procedures conducted by the urologists adopting this technique may potentially incur a higher risk of negative outcomes or complications.

A need exists in the art for a laser surgical device designed to reduce the multi-tasking of a physician performing a laser surgical procedure, as well as to introduce reliable and repeatable movements of the laser fiber which will optimize patient outcomes and increase urologist satisfaction.

SUMMARY OF THE INVENTION

In one aspect, the present invention provides a laser surgery device to rotate a laser fiber along a longitudinal axis of the laser fiber. In this aspect, the device includes a hollow inner cylinder nested within a hollow outer case. The inner cylinder is rotatably connected to the outer case, the rotational axis of the interior cylinder is aligned with the central axis of the outer case, and the hollow inner cylinder includes an inner surface that defines a laser fiber lumen. The laser fiber lumen forms a channel in which the laser fiber is detachably held, and the laser fiber protrudes from laser fiber lumen at a device exit. The device also includes a motor and power source operatively connected to the inner cylinder such that the inner cylinder rotates in a first direction and a second direction when the motor is in operation. The device additionally includes a rotation speed control operatively connected to the motor, and a rotation sweep control operatively connected to the motor.

In another aspect, a laser surgery device is provided to releasably hold a surgical laser apparatus that includes a laser fiber and a control knob in a fixed position and to rotate the laser fiber in a predefined repeating pattern. The device includes a hollow inner cylinder nested within a hollow outer case. The inner cylinder is rotatably connected to the outer case, the rotational axis of the interior cylinder is aligned with the central axis of the outer case, and the hollow inner cylinder includes an inner surface that defines a control knob lumen and a laser fiber lumen. The control knob lumen opens to a device entry at one end and to the laser fiber lumen at the opposite end. The laser fiber lumen opens to a device exit at one end and to the control knob lumen at the opposite end. The control knob lumen is contoured to detachably hold the control knob. The laser fiber lumen forms a channel through which the laser fiber may be threaded from the control knob lumen to the device exit. The device also includes a motor operatively connected to a power source. The motor is operatively connected to the inner cylinder such that the inner cylinder rotates in a first direction and in a second direction when the motor is in operation. The device further includes a rotation sweep control and a rotation speed control that are both operatively connected to the motor. The device additionally includes a support assembly that includes an elongated support arm, a clamp attached to one end of the support arm, and an attachment assembly on the opposite end of the support arm. The clamp is attached to a working channel of a laser cystoscope and the attachment assembly also includes an attachment fitting and a releasable latch. Alternatively, the clamp may attach to other parts of the cystoscope.

Another aspect provides a laser surgery device to detachably receive a surgical laser that includes a laser fiber, a control knob, and a shielded laser fiber connecting the laser fiber to a laser source. The device includes a hollow outer case that includes an exterior surface, an interior surface, an upper casing, and a lower casing. The upper casing and the lower casing are hingeably connected along one line of intersection by two or more hinges attached to the exterior surface. The upper casing and lower casing are reversibly secured diametrically opposite to the two or more hinges by at least one latch attached to the exterior surface. The interior surface defines a main lumen extending along the longitudinal axis of the outer cylinder. The device further includes a hollow inner cylinder situated within the main lumen and rotatably connected to the interior surface of the outer case such that the axis of rotation of the inner cylinder coincides with the longitudinal axis of the outer case. The inner cylinder includes an inner surface, an outer surface, an upper member, and a lower member. The upper member is attached to the upper casing and the lower member is attached to the lower casing when the outer cylinder is in an open position. The inner surface defines the walls of a laser lumen fitted to the external shape of the laser fiber, control knob, and shielded laser fiber. The shielded laser fiber, control knob, and laser fiber may be placed within the inner cylinder such that the laser fiber emerges from one end of the surgical laser lumen and the shielded laser fiber emerges from the opposite end of the surgical laser lumen. The upper member and lower member reversibly clamp the surgical laser within the inner cylinder when the outer case is latched in a closed position.

In this same aspect the device additionally includes an electrical motor that includes a driveshaft protruding from a motor unit. The motor unit is attached to the interior surface of the outer case. The device also includes a power source electrically connected to the motor, a drive gear attached to the end of the driveshaft opposite to the motor unit, and a transmission gear attached to the outer surface of the inner cylinder. The transmission gear meshes with the drive gear. In addition, the device includes a motor sweep control circuit electrically connected to the electrical motor and a motor speed control circuit electrically connected to the electrical motor.

In yet another aspect, a laser surgery device is provided that includes an entry and an exit. In this aspect, the device may detachably receive and hold a laser fiber and control knob. The device also includes a hollow outer case that includes an exterior surface and an interior surface. The interior surface forms the walls of a cylindrical main lumen, which opens to the entry at one end and to the exit at the opposite end. The interior surface includes at least two circumferential outer depressions forming the sides of at least two circumferential outer bearing channels spaced along the longitudinal axis of the outer case. A plurality of bearings is situated within each of the at least two outer bearing channels such that the bearings are free to roll in a circumferential direction along the outer bearing channels.

In this same aspect, the device additionally includes a hollow inner cylinder centered within the main lumen. The main lumen includes an inner surface and an outer surface. The outer surface includes at least two circumferential inner indentations forming the sides of at least two inner bearing channels. Each inner bearing channel is aligned with one of the outer bearing channels such that the plurality of bearings are enclosed by one of the inner bearing channels from below and one of the outer bearing channels from above. The inner cylinder rotates freely within the outer case on the plurality of bearings.

Also in this same aspect, the device includes a transmission gear that includes a plurality of transmission gear teeth. The transmission gear is attached to the outer surface of the inner cylinder such that the inner cylinder passes through the center of the transmission gear along the rotational axis of the transmission gear. The device additionally includes an electrical motor that includes a driveshaft protruding from a power unit. The power unit is attached to the interior surface of the outer case.

The device provided in this same aspect additionally includes a drive gear that includes a plurality of drive gear teeth operatively engaged with the cylinder gear teeth. The drive gear is attached to the free end of the driveshaft through the center of the drive gear, and the rotational axis of the drive gear is parallel to the longitudinal axis of the inner cylinder. The device also includes a motor sweep control operatively connected to the motor, a motor speed control operatively connected to the motor and to the motor sweep control, a power source connected to the motor via the motor sweep control unit and the motor speed control unit, and a laser fiber securing plug that includes a cylindrical plug body, a ratchet catch, and an insertion arm.

In this same aspect, the plug body inserts into a control knob lumen defined by the inner surface of the inner cylinder. The control knob lumen opens to the device entry. The cylindrical plug body includes an insertion end, a removal end opposite the insertion end, an upper plug surface that includes a longitudinal sector of the plug body, a lower plug surface situated diametrically opposite to the upper plug surface that includes a longitudinal sector of the plug body, and a narrow radial notch extending longitudinally along the entire plug body and extending radially from the central longitudinal axis of the plug body through the lower plug surface. The ratchet catch includes at least one retractable tooth attached in a longitudinal pattern along the upper plug surface. The retractable tooth may engage a plurality of ratchet teeth formed in a longitudinal pattern by the inner surface of the inner cylinder at the upper region of the inner cylinder. The insertion arm includes an elongated member attached at one end to the removal end of the plug body. The insertion arm is mechanically engaged to the ratchet catch such that the ratchet catch may be reversibly retracted by applying a lateral inward force to the insertion arm.

In this aspect, the device also includes an amount of compressible material situated within a cylindrical laser fiber lumen defined by the inner surface of the inner cylinder. One end of laser fiber lumen opens to the control knob lumen at the end of the control knob lumen opposite to the device entry, and the opposing end of the laser fiber lumen opens to the device exit. The device also includes a reference nub that includes a narrow fin-shaped projection attached to the exterior surface along the longitudinal axis and projecting radially outward. The device additionally includes a motor sweep control switch mounted on the external surface of the outer case which is electrically connected to the motor sweep control circuit, and a motor speed control switch mounted on the external surface of the outer case which is electrically connected to the motor speed control circuit.

Yet another aspect provides a method of performing a laser surgical procedure that includes providing a laser surgery system that includes a laser source operatively connected to a surgical laser fiber which protrudes from an outer case. The outer case includes an exterior surface, a rotation speed control situated on the exterior surface, and a rotation sweep control situated on the exterior surface. The method also includes threading the surgical laser fiber through a working channel of an endoscopic surgical device into a surgical site, activating the rotation speed control and the rotation sweep control to initiate a rotational movement of the surgical laser fiber about the longitudinal axis of the laser fiber, and activating the laser source to initiate the release of laser energy from the laser fiber into the surgical site.

Still another aspect provides a method of performing a laser surgical procedure that includes providing a surgical laser fiber protruding from a control knob and providing a laser surgery device that includes an outer case having an exterior surface, an entrance, an exit, and an inner cylinder defining a control knob lumen opening to the entrance at one end and to a laser fiber lumen at the opposite end. The laser fiber lumen opens to the exit at one end and to the control knob lumen at the opposite end. The laser surgery device further includes a securing plug, and a rotation speed control and a rotation sweep control situated on the exterior surface.

In this same aspect, the method also includes threading the surgical laser fiber through the laser fiber lumen from the entrance, such that the control knob is situated within the control knob lumen and the laser fiber passes through the laser fiber lumen and protrudes from the exit. The method further includes inserting the securing plug into the control knob lumen from the entrance such that the securing plug is situated in the control knob lumen between the control knob and the entrance, and threading the surgical laser fiber protruding from the exit through a working channel of an endoscopic surgical device into a surgical site. The method additionally includes activating the rotation speed control and the rotation sweep control to initiate a rotational movement of the surgical laser fiber about the longitudinal axis of the laser fiber, and activating the laser source to initiate the release of laser energy from the laser fiber into the surgical site.

Still another aspect provides a method of performing a laser surgical procedure that includes providing a surgical laser fiber protruding from a control knob and providing a laser surgery device. The laser surgery device includes an outer case with an exterior surface, an entrance, an exit, an upper casing hinged to a lower casing, and a latch diametrically opposite to the hinge line between the upper casing and the lower casing. In addition, the laser surgery device includes an inner cylinder rotatably attached to the outer case. The inner cylinder includes an upper member, a lower member, and an internal surface. The upper member is attached to the upper casing and the lower member is attached to the lower casing, such that the internal cylinder opens when the outer case is opened. The internal surface defines a control knob lumen opening to the entrance at one end and to a laser fiber lumen at the opposite end. The laser fiber lumen opens to the exit at one end and to the control knob lumen at the opposite end. When the laser surgery device is in a closed position, the internal cylinder rotates about the longitudinal axis of the laser fiber. The laser surgery device additionally includes a rotation speed control and a rotation sweep control installed on the exterior surface.

In this same aspect, the method further includes opening the latch and separating the upper casing and lower casing, placing the control knob into the control knob lumen in the lower member and placing the surgical laser fiber into the laser fiber lumen in the lower member such that the laser fiber protrudes from the exit, as well as closing the upper casing and lower casing and securing the outer case with the latch. The method additionally includes threading the surgical laser fiber protruding from the exit through a working channel of an endoscopic surgical device to a surgical site, activating the rotation speed control and the rotation sweep control to initiate a rotational movement of the surgical laser fiber about the longitudinal axis of the laser fiber, and activating a laser source operatively connected to the surgical laser fiber to initiate the release of laser energy from the surgical laser fiber into the surgical site.

Other aspects of the invention are described in detail below.

BRIEF DESCRIPTION OF THE DRAWINGS

FIG. 1A is a cross-sectional view of an outer sheath of a cystoscope.

FIG. 2 is a perspective view of the insertion of a laser fiber into a laser surgery device.

FIG. 3A is a perspective view of the insertion of a securing plug into a laser surgery device.

FIG. 3B is a perspective view of an assembled laser surgery device.

FIG. 10 is a perspective view of the entry of a laser surgery device with a clamshell outer casing.

FIG. 11 is a perspective view of the exit of a laser surgery device with a clamshell outer casing.

FIG. 12 is a longitudinal cross-sectional view of a laser surgery device with a clamshell outer casing.

FIG. 15 is a detailed side view of a laser surgery device attached to a cystoscope.

FIG. 16 is a cross-sectional view of a support arm with a hinge and a clamp fitting.

FIG. 17 is a cross-sectional view of the attachment of a support arm to a laser surgery device.

FIG. 18 is a cross-sectional view of a support arm attachment fitting mounted in a support arm attachment receptacle.

FIG. 21 is a longitudinal cross-sectional view of a laser surgery device with an integrated stepper motor.

FIG. 22 is a cross-sectional view of the laser surgery device with the integrated stepper motor showing an integrated gear and four integrated electromagnets.

DETAILED DESCRIPTION OF THE INVENTION

The present invention relates to laser surgery devices and methods of performing laser surgery using a laser surgery device. More specifically, the present invention provides a laser surgery device to rotate a surgical laser fiber about the longitudinal axis of the laser fiber. The laser surgery device may rotate the laser fiber in a first direction and in a second direction. The rotation may be in a repeating pattern in which the laser fiber rotates clockwise and then counter-clockwise through a user-specified sweep angle and an essentially constant rotation rate.

The device is designed for use with an endoscopic device including but not limited to cystoscope, colonoscope, gastroscope, proctoscope, rhinoscope, bronchoscope, otoscope, gynoscope, laparoscope, arthroscope, thoracoscope, mediastinoscope, amnioscope, and panendoscope. In an exemplary embodiment, the endoscopic device is a cystoscope. For purposes of illustration, the laser surgery device used with a cystoscope is described herein.

In general, the device is typically constructed from materials capable of undergoing sterilization procedures without diminishing in function. Non-limiting examples of suitable construction materials for the device include heat resistant plastics including polyetheretherketones, polyetherimides, phenol formaldehydes, and polytetrafluoroethylenes, and metals including stainless steel, aluminum, titanium, and alloys thereof.

Detailed descriptions of various aspects of the device, as well as methods of using the device to perform laser surgeries are provided below.

I. Overview

Figure 1:
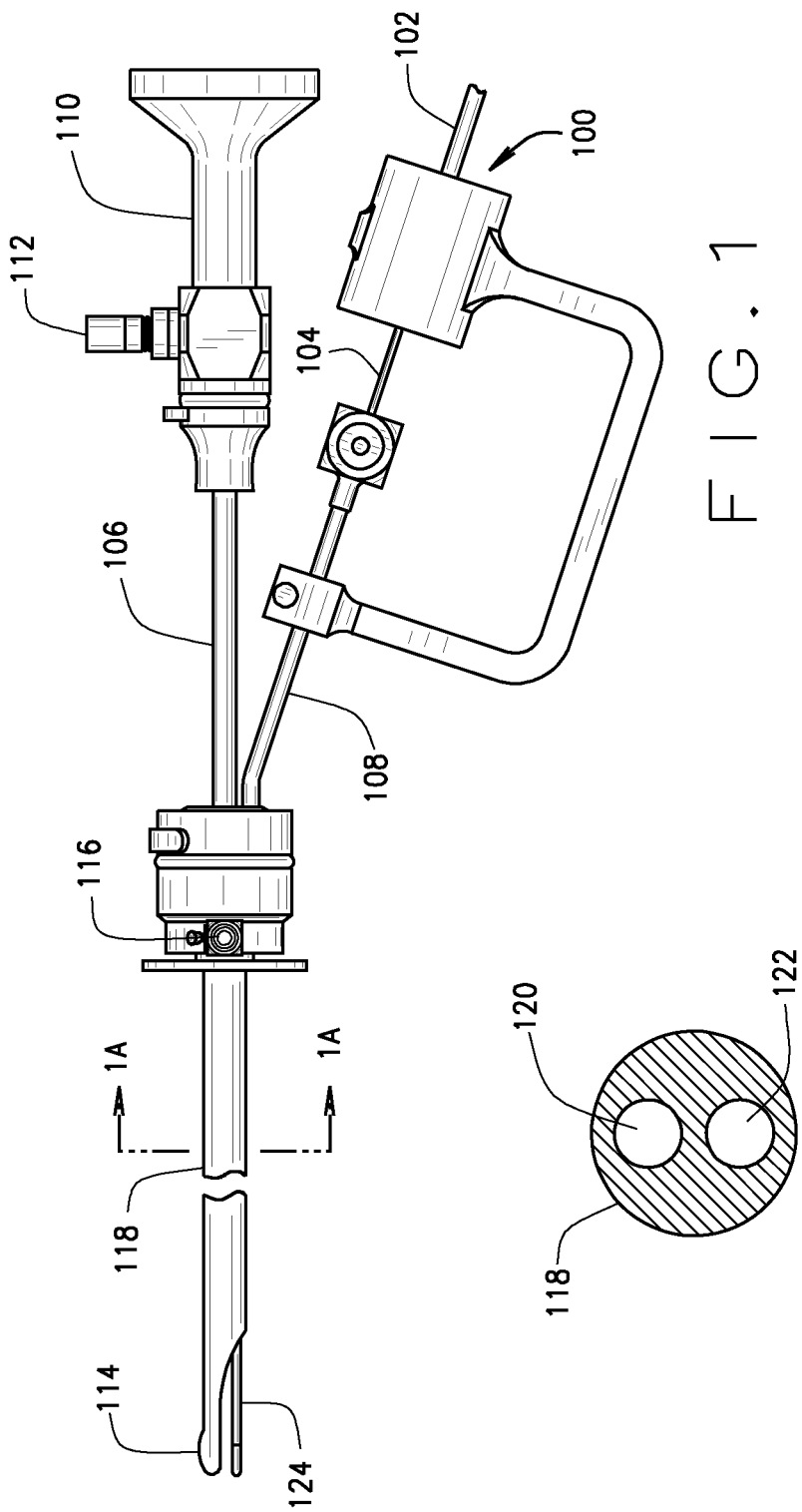
FIG. 1 is a side view of a laser surgery device attached to a cystoscope.

Referring to FIG. 1, a device 100 is shown along with a cystoscope 106. To conduct laser surgery, a distal end 114 and an outer sheath 118 of the cystoscope 106 are inserted through the urethra of a patient to situate a laser fiber tip 124 in the vicinity of a surgical site, for example the prostate gland. The cystoscope 106 includes optics 110 to view a surgical area in which the laser surgery is performed. The surgical site is illuminated by a fiber optic cable (not shown) through a light guide 112 and an optics channel 120 located within the outer sheath 118.

Irrigation fluid may be provided to fill the bladder prior to performing surgery and to irrigate the surgical site during the surgical procedure by way of an irrigation water inlet (not shown) that introduces fluid through the outer sheath 118 of the cystoscope 106. The irrigation fluid is drained via an irrigation fluid outlet 116.

A laser fiber 104 is inserted through a working channel 108 and a laser fiber channel 122 so that a laser fiber tip 124 protrudes from the distal end 114 of the cystoscope 106. In use, the laser fiber tip 124 directs laser energy downward and away from the distal end 114, causing the vaporization, ablation, and/or cauterization of tissues in the surgical site.

The device 100 fits over the laser fiber 104 and may optionally connect to the outside of the working channel 108. The laser fiber 104 protrudes from one end of the device 100. The laser fiber 104 is connected to a laser source (not shown) via a shielded laser fiber 102, which protrudes from the opposite end of the device 100. The device 100 may optionally fasten to cystoscope 106, for example on the outside of the working channel 108 as shown in FIG. 1.

In use, the device 100 is activated, causing the laser fiber tip 124 to rotate about its longitudinal axis. In one aspect, the laser fiber tip 124 rotates clockwise and then counterclockwise through a user-specified sweep angle at an essentially constant and user-specified speed. The surgeon may adjust the speed and/or sweep angle of the laser fiber tip 124 during rotation of the laser fiber 104.

The device 100 may be held in the hand of the surgeon during rotation of the laser fiber 104. Alternatively, as shown in FIG. 1, the device 100 may be fastened in place for hands-free operation of the device 100 during surgery.

The device 100 may slide over the laser fiber 104, as shown in FIGS. 1-4 in order to mechanically connect the device 100 to the laser fiber 104. Alternatively, the device 100 may open in a clamshell fashion to fit over the laser fiber 104, as shown in FIGS. 10-14.

II. Description of Laser Fiber

The insertion of the laser fiber 104 into the device 100 is shown in FIG. 2. The laser fiber 104 is a continuous fiber optic cable that ends at the laser fiber tip 124. The laser fiber tip 124 includes a lens (not shown) that directs laser energy in a narrow beam or cone to the tissue on the surgical site. The laser fiber tip 124 may also include markings to indicate the orientation of the laser fiber 104, for example to indicate the direction in which the laser energy is directed.

A control knob 202 may be attached to the laser fiber 104 such that the laser fiber 104 threads through the center of the control knob 202. Typically the control knob 202 is approximately cylindrical in shape, with the laser fiber 104 running through the central axis of the control knob 202. At the end of the control knob 202 opposite to the laser fiber 104, a shielded laser fiber 102 attaches to the laser fiber 104. The shielding typically ends at the control knob 202 at the point of insertion of the laser fiber 104 into the control knob 202.

The control knob 202 may also include a thumb knob 212 that indicates the orientation of the laser fiber 104. When used without the device 100, the control knob 202 is rotated about its longitudinal axis in order to rotate the laser fiber 104 during surgery. The thumb knob 212 helps to assess the extent of the sweep angle applied to the laser fiber 104 by the surgeon.

The control knob 202 may also include textural features to facilitate gripping the control knob 202 while rotating the control knob 202 during a surgical procedure. For example, the control knob 202 may include a plurality of raised knurls 220 separated by depressions 218 on the surface of the control knob 202. The knurls 220 and depressions 218 may run longitudinally along the entire length of the control knob, as illustrated in FIG. 2.

III. Description of Device

Figure 5:
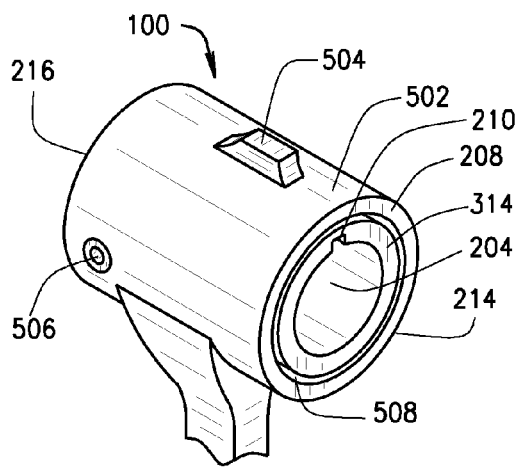
FIG. 5 is a perspective view of the entry of a laser surgery device.

Referring to FIG. 5, the device 100 includes a hollow inner cylinder 314 rotatably connected to a hollow outer case 208 such that the inner cylinder 314 rotates about its longitudinal axis within the outer case 208. The inner cylinder 314 surrounds a control knob lumen 204 that is contoured to receive the control knob 202 (not shown). The control knob lumen 204 includes a notch 210 at its upper portion, shaped to accommodate the thumb knob 212 of the control knob 202. The device 100 also includes an entrance 214 in which the laser fiber 104 is inserted, and a device exit 216 from which the laser fiber 104 protrudes when mounted in the device 100.

The outer case 208 forms an exterior surface 502 that may be smooth or textured to facilitate gripping the device 100 during rotation of the laser fiber 104. A reference nub 504 is attached to the upper part of the exterior surface 502 to indicate the orientation of the device 100. The reference nub 504 is typically a fin-shaped projection that extends radially outward from the exterior surface 502 of the device 100. The reference nub 504 is typically centered along the length of the outer case 208, although the reference nub 504 may be located anywhere on the outer case. The reference nub 504 may range in length between about 5% and 100% of the total length of the outer case 208.

The device 100 may further include an optional recharging outlet 506 mounted on the outer case 208. The recharging outlet 506 is electrically connected to a power source 728 (not shown) inside of the device 100. A connector plug of a power cord connected to an electrical power outlet of an electrical utility grid (not shown) may be inserted into the recharging outlet 506 to recharge the power source 728 (not shown). After charging the power source 728, the connector plug of the power cord may be disconnected from the recharging outlet 506 for wireless use of the device 100.

Figure 6:
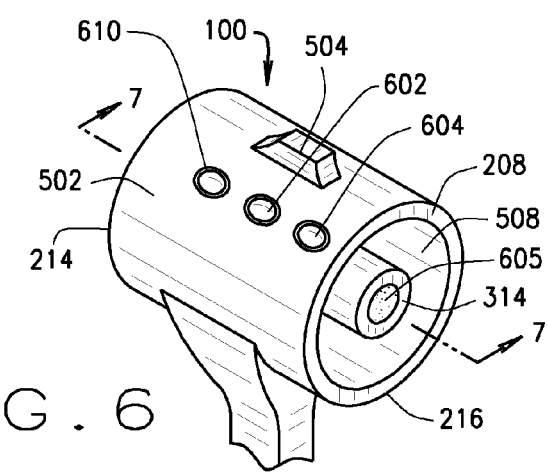
FIG. 6 is a perspective view of the exit of a laser surgery device.

Referring to FIG. 6, the outer case 208 further defines a main lumen 508 within which the inner cylinder 314, and other components of the device 100 such as the motor 725 (not shown) are contained. The device 100 may further include a power control 610, a rotation speed control 602 and a rotation sweep control 604 installed on the exterior surface 502. The power control 610 is an electrical switch that opens and closes the electrical connection between the power source 728 (not shown) and the motor 725 (not shown). The rotation speed control 602 is an electrical switch that is electrically connected to the motor speed control circuit 732 (not shown), and the rotation sweep control 604 is an electrical switch that is electrically connected to the motor sweep control circuit 734 (not shown). The rotation speed control 602 and the rotation sweep control 604 may include any type of electrical switch known in the art. The rotation speed control 602 and the rotation sweep control 604 may be implemented as two separate switches, or the function of both controls may be implemented as a single switch. Non-limiting examples of suitable electrical switches include pushbuttons, toggles, membrane switches, variable resistance switches, DIP switches, and knife switches.

The electrical switches may be selected to provide feedback to the user to indicate the current switch settings using any feedback mechanism known in the art. For example, the switch may be a dial or slider switch that moves past a series of markings printed on the outer case 208 to visually indicate the control setting of the switch. The switch may optionally incorporate a visual display such as a series of one or more LEDs in a line that illuminate in a pattern such as a bar of increasing length, or by changing color or brightness, to indicate the setting of the switch. The device 100 may encode the switch settings as an electrical or electromagnetic signal that may be received and superimposed onto the image of the surgical area viewed by the optics 110.

The switch may be a toggle switch that indicates a switch setting by one or more discrete tactile clicks and optionally a change in the position of an end of the switch. The switch may signal its position by vibrating in one or more pulses that change in the vibration frequency of each pulse, the frequency of pulses per second, the magnitude of the vibration, and any combination thereof. The switch may signal its position by variation in the force required to change the switch setting to a different position. For example, a switch may require a higher force to move to its most extreme setting. The switch may change the physical size or shape of the device 100 to indicate the switch setting.

Alternatively, an auditory feedback mechanism may be used to indicate the setting of a control switch. The switch may emit one or more auditory tones that change in pitch, loudness, frequency of tones per second, and any combination thereof to indicate the position of the switch.

The rotation speed control 602 may command at least one or more discrete rotation speeds for the laser fiber 104, or the rotation speed control 602 may command a continuous range of rotation speeds. The rotation speed control 602 may command a range of rotation speeds ranging from about 5°/second to about 360°/second.

The rotation sweep control 604 may command at least one or more discrete sweep angles for the laser fiber 104 or the rotation sweep control 604 may command a continuous range of sweep angles. Sweep angles, as defined herein, are specified as a maximum angle of rotation of the laser fiber 104 clockwise or counterclockwise relative to a vertical reference plane. The rotation sweep control 604 may command a range of sweep angles ranging from about 5° to about 180° clockwise and counterclockwise relative to a vertical reference plane. The rotation sweep control 604 may command a range of sweep angles ranging from about 30° to about 90° clockwise and counterclockwise relative to a vertical reference plane.

Optionally mechanical stops may be included that limit the sweep range to a within a desired angular range of travel. The mechanical stops may prevent the laser fiber 104 from moving to a position in which the laser fiber tip 124 or any part of the cystoscope 106 may be damaged while the laser is operational. The function of the mechanical stops may also be implemented by using the motor control circuits to cut power to the motor 725 to prevent movement of the laser fiber 104 to undesired positions.

The device 100 may optionally include a compressible material 606 situated within the laser fiber lumen 605 (not shown) to hold the laser fiber 104 (not shown) in place during rotation of the laser fiber 104. The compressible material 606 is selected to maintain the laser fiber 104 near the center of the cross-section of the working channel 108 without imparting a significant amount of friction to the laser fiber 104. The compressible material typically contains a small passageway through which the laser fiber 104 may pass or forms a passageway for the laser fiber 104 as the laser fiber 104 is threaded through the working channel 108 (not shown). Any suitable material may be used as the compressible material including but not limited to natural rubber, synthetic polyisoprene, butyl rubber, polybutadiene, styrene-butadiene rubber, nitrile rubber, chloroprene rubber, polychloroprene, ethylene propylene rubber, ethylene propylene diene rubber, epichlorohydrin rubber, polyacrylic rubber, silicone rubber, fluorosilicone rubber, polyether block amides, chlorosulfonated polyethylene, ethylene-vinyl acetate, and combinations thereof.

Figure 7:
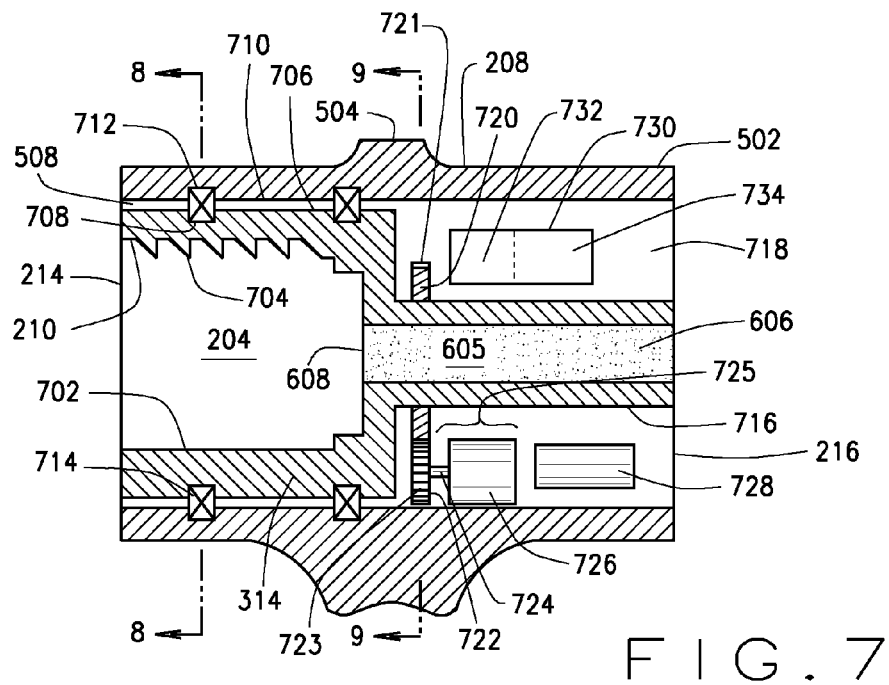
FIG. 7 is a longitudinal cross-sectional view of a laser surgery device.

FIG. 7 shows a cross-sectional view of the device 100. The outer case 208 includes an exterior surface 502 and an interior surface 710. The interior surface 710 defines a main lumen 508 containing the inner cylinder 314 and other device components. The inner cylinder 314 includes an inner surface 702 and an outer surface 706. The inner cylinder 314 typically has a larger outer diameter near the entrance 214 to accommodate the control knob lumen 204, and contracts to a smaller outer diameter in the region 716 containing the laser fiber lumen 605. An inner compartment 718 is defined between the interior surface 710 of the outer case 208 and the outer surface 706 of the inner cylinder 314.

The interior surface 710 of the outer case 208 further includes two or more circumferential outer depressions forming the walls of two or more outer bearing channels 712. A plurality of bearings 714 are situated within each of the at least two outer bearing channels 712. Similarly, the outer surface 706 of the inner cylinder 314 includes two or more circumferential depressions forming the walls of two or more inner bearing channels 708. Each of the at least two inner bearing channels 708 is aligned with each of the corresponding outer bearing channels 712. The plurality of bearings 714 are free to roll along the circumferential enclosures formed between each inner bearing channel 708 and each outer bearing channel 712, thereby rotatably connecting the inner cylinder 314 to the outer case 208.

The inner surface 702 of the inner cylinder 314 forms a control knob lumen 204. The upper region of the inner surface 702 may optionally form two or more ratchet teeth 704 that are shaped to interlock with the ratchet catch 306 of the securing plug 300 (not shown). The inner surface 702 also forms the laser fiber lumen 608 optionally filled with an amount of compressible material 606; the laser fiber lumen 608 opens into the control knob lumen 204 and to the device exit 216 at opposing ends.

The device 100 further includes a motor 725 that includes a driveshaft 724 protruding from a power unit 726. The rotational axis of the driveshaft 724 is in parallel alignment with the longitudinal axis of the inner cylinder 314. The power unit 726 is attached to the interior surface 710 of the outer case 208.

Any suitable power unit 726 known in the art may be utilized in the device 100 so long as the power unit 726 is capable of producing sufficient power within the space of the inner compartment 718 using power sources commonly available in an operating room, including but not limited to electrical power or compressed air. Further, the power unit 726, like the other components of the device 100, must be capable of withstanding the conditions of sterilization without losing operational capability. The power unit 726 may be reversible to simplify the design and operation of the device 100. Non-limiting examples of suitable power units 726 include stepper motors, DC electric motors, AC electric motors, pneumatic motors, and hydraulic motors. In an exemplary embodiment, the power unit 726 is a stepper motor.

A drive gear 722 is connected the free end of the driveshaft 724 opposite to the power unit 726 through the center of the drive gear 722 such that the rotational axis of the drive gear 722 is coincident with the rotational axis of the driveshaft 724. The drive gear 722 includes at least two or more drive gear teeth 723 that mesh with at least two or more transmission gear teeth 721 of a transmission gear 720. The transmission gear 720 is attached to the outer surface 706 of the inner cylinder 314 such that the axis of rotation of the transmission gear 720 is coincident with the longitudinal axis of the inner cylinder 314. The laser fiber lumen 605 passes through the center of the drive gear 722. The drive gear teeth 723 and transmission gear teeth 721 mesh to form an operative connection between the motor 725 and the inner cylinder 314.

The inner compartment 718 further contains a power source 728 that is operatively connected to the motor 725. Any suitable power source 728 known in the art may be used in the device 100 so long as the power source 728 is compatible with the requirements of the motor 725. Non-limiting examples of suitable power sources 728 include a compressed air source, a hydraulic pressure source, an AC power supply, a DC power supply, a battery, and a rechargeable battery. In an exemplary embodiment, the power source 728 is a rechargeable electric battery. The use of batteries and rechargeable batteries provides for wireless operation of the device 100.

Motor control circuitry 730 is situated within the inner compartment 718. The motor control circuitry 730 includes a motor speed control circuit 732 operatively connected to the rotation speed control 602 (not shown), and a motor sweep control circuit 734 operatively connected to the rotation sweep control 604 (not shown). Optionally, the motor control circuitry 730 may also include a laser fiber extension/retraction control circuit (not shown) operatively connected to a longitudinal control (not shown).

Any suitable control circuit components known in the art may be used in the device 100, so long as the control circuit components are appropriate for the type of power unit 726 selected for the device 100. Non-limiting examples of suitable motor speed control circuits 732 include variable resistors, torque converters, valves, transistors in an H-bridge configuration, SCR controls, PWM controls, MOSFETs, diodes, and switches. Non-limiting examples of suitable motor sweep control circuits 734 include transistors in an H-bridge configuration, position sensors with switches, servos with switches connected to position feedback sensors, diodes, and relays. Alternatively, the motor control circuitry 730 may be implemented as an integrated circuit or as a microprocessor.

Figure 8:
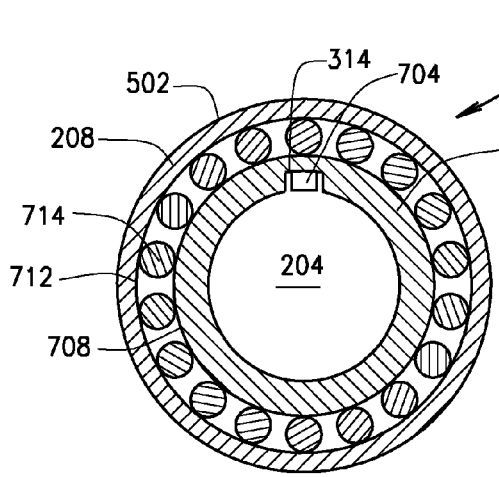
FIG. 8 is a cross-sectional view of a laser surgery device through a bearing channel.

FIG. 8 shows a cross-section of the device 100 through one of the outer bearing channels 712 and associated inner bearing channel 708. The bearings 714 are free to roll circumferentially, allowing the inner cylinder 314 to rotate relative to the outer case 208.

Figure 9:
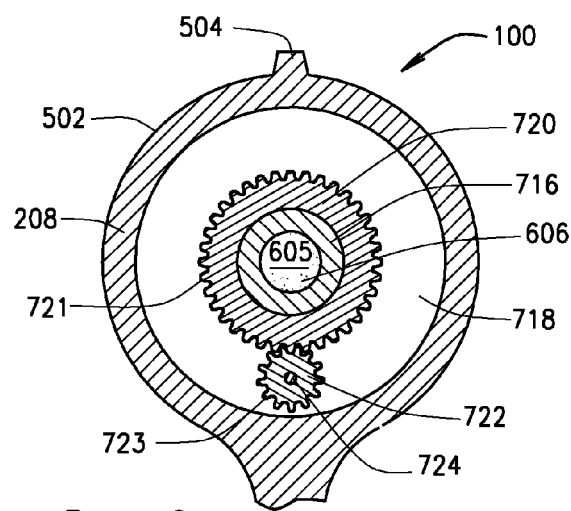
FIG. 9 is a cross-sectional view of a laser surgery device through a drive gear and transmission gear.

FIG. 9 shows a cross-section of the device 100 through the drive gear 722 and the transmission gear 720, in which the drive gear teeth 723 are meshed with the transmission gear teeth 721 within the inner compartment 718. When the driveshaft 724 of the motor 725 turns the drive gear 722, the drive gear 722 turns the transmission gear 720, thereby causing the inner cylinder 314 to rotate within the outer case 208.

Referring to FIG. 10, the device 100A may include at least two hinges 1002 rotatably joining the upper casing 1004 and the lower casing 1006 along a hinge line. The inner cylinder 314 may be divided into an upper member 1008 that is operably attached to the upper casing 1004 and a lower casing 1006 that is operably attached to the lower casing 1006. The control knob lumen 204 may have a diameter sized to accommodate the shielded laser fiber 102 (not shown) near the entrance 214. The laser fiber 104 (not shown) and the control knob 202 (not shown) are placed within the laser fiber lumen 605 (not shown) and the control knob lumen 204 (not shown), respectively, when the upper casing 1004 and the lower casing 1006 are separated, placing the device 100A in an open position.

Referring to FIG. 11, once the laser fiber 104 (not shown) and the control knob 202 (not shown) are placed within the device 100A, the upper casing 1004 and the lower casing 1006 are rotated together and secured with a latch 1102 that is mounted on the exterior surface 502 of the outer case 208, situated diametrically opposite to the hinge line.

FIG. 12 is a cross section of the device 100A, showing the lower half of the device 100A including the lower casing 1006. In order to align the upper casing 1004 (not shown) with the lower casing 1006, the lower casing 1006 includes at least two or more alignment peg receptacles 1202 to receive the corresponding alignment pegs 1402 (not shown) included in the upper casing 1004 (not shown). To properly align the upper member 1008 (not shown) with the lower member 1010, the lower member 1010 also contains at least two or more alignment peg receptacles 1202 that receive the corresponding alignment pegs 1402 included in the upper member 1008.

Figure 13:
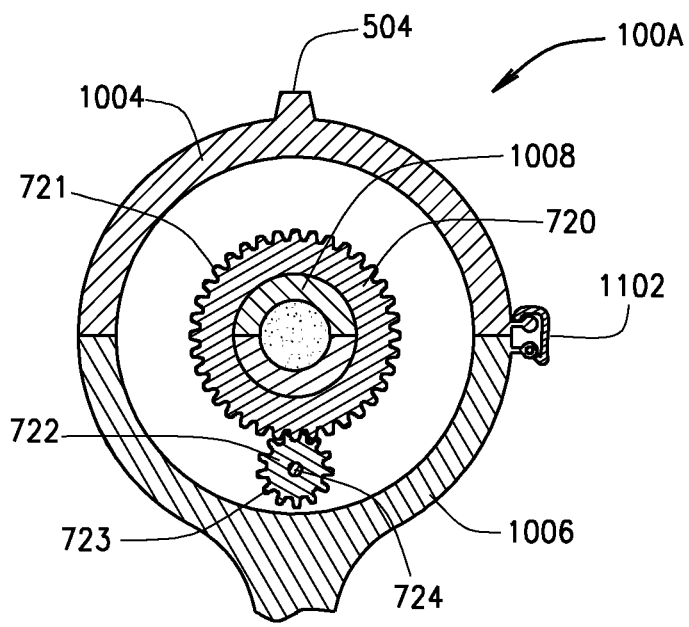
FIG. 13 is a cross-sectional view of a laser surgery device with a clamshell outer casing through a drive gear and transmission gear.

FIG. 13 is a cross-section through the latch 1102 of the device 100A, showing the upper casing 1004 and lower casing 1006 secured together by the latch 1102. The latch 1102 may be any releasable fastener mechanism known in the art that draws the upper casing 1004 toward the lower casing 1006 as the latch is fastened in order to firmly clamp the laser fiber 104 (not shown) and control knob 202 (not shown) inside the device 100A in its closed position. Non-limiting examples of suitable latches 1102 include knuckle catches, rotary catches, tension catches, magnetic catches, and draw latches. In an exemplary embodiment, the latch 1102 is a draw latch.

The latch 1102 may be surface-mounted on the exterior surface 502, or parts of the latch 1102 may be formed from the material of the outer case 208 in the region where the edges of the upper casing 1004 and lower casing 1006 meet diametrically opposite to the two or more hinges 1002, as shown in FIG. 13.

Figure 14:
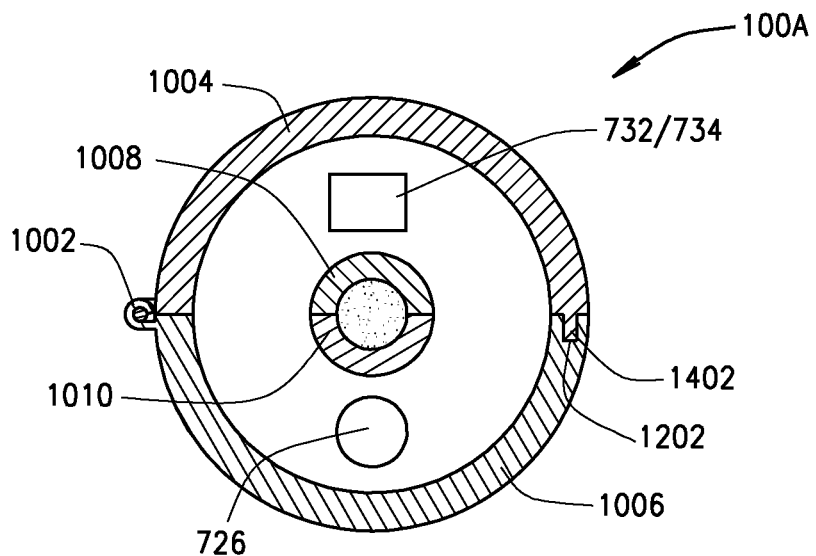
FIG. 14 is a cross-sectional view of a laser surgery device with a clamshell outer casing through a hinge and a latch.

FIG. 14 is a cross-section through the device 100A through one of the hinges 1002. One of at least two alignment pegs 1402 are situated diametrically opposite to a hinge 1002 in FIG. 14. The alignment peg 1402 protrudes downward from the edge of the upper casing 1004 and fits into an alignment peg receptacle 1202 that is inset into the edge of the lower casing 1006. Fitting the alignment pegs 1402 into the corresponding alignment peg receptacles 1202 aligns the upper casing 1004 with the lower casing 1006 and aligns the upper member 1008 with the lower member 1010 when the device 100A is in the closed position.

The alignment peg 1402 may protrude upwards from the edge of the lower casing 1006 and fit into an alignment peg receptacle 1202 that is inset into the edge of the upper casing 1004. Alternatively, a ridge protruding from the edge of the upper casing 1004 may fit into a groove cut into the edge of the lower casing 1006. The edge of the upper casing 1004 may optionally include notches or scallops that fit into corresponding shapes cut into the edge of the lower casing 1006.

Referring to FIG. 15, a support arm 1502 may be used to attach the device 100 to the working channel 108, allowing the hands-off operation of the device 100 during surgery. The support arm 1502 is typically an elongated structure that includes a clamp fitting 1504 on one end, and a support arm receptacle 1508 on the opposite end.

The clamp fitting 1504 attaches the support arm 1502 to some part of the cystoscope 106, for example the exterior of the working channel 108 as shown in FIG. 15. The clamp fitting 1504 may be firmly attached by twisting a tightening screw 1506. Any clamping mechanism known in the art may be used to secure the support arm 1502 to the working channel 108, including but not limited to band clamps, bar clamps, Cardellini clamps, C-clamps, magnetic clamps, handscrew clamps, vise-grip clamps, and toggle clamps.

The support arm receptacle 1508 removably attaches the support arm 1502 to the device 100. Any removable attachment device known in the art may be used including but not limited to clamping mechanisms, latching mechanisms, screw fitting mechanisms, magnetic coupling mechanisms, and Velcro mechanisms. As shown in FIG. 15, the support arm receptacle 1508 may be a socket contoured to accommodate a support arm attachment fitting 1510. The support arm 1502 is attached to the exterior surface 502 of the outer case 208 (not shown). The support arm 1502 may further include a quick release lever 1512 that locks the support arm attachment fitting 1510 into the support arm receptacle 1508. Any attachment mechanism may be used so long as the device 100 may be quickly and easily removed during rotation of the laser fiber 104 with minimal mechanical disruption to the device 100 or the laser fiber 104 (not shown). By actuating the quick release lever 1512, the support arm 1502 may be disengaged from the device 100 such that the physician may manually hold the device 100 while the device 100 provides the rotation to the laser fiber 104.

The support arm 1502 may optionally include a support arm hinge 1514 designed and located to swing the support arm receptacle 1508 away from the device 100 and the cystoscope 106 when the support arm 1502 is detached from the device 100.

FIG. 16 is a cross section of the support arm 1502 taken through the clamp fitting 1504 and support arm hinge 1514. The clamp fitting 1504 may include a stationary arm 1602 as well as an adjustable arm 1604 that pivots on a hinge 1606. The clamp fitting 1504 is placed around the working channel 108 and the adjustable arm 1604 is tightened toward the stationary arm 1602 by rotating the tightening screw 1506. The tightening screw passes through a flange 1610 containing an unthreaded opening 1620 sized to receive the tightening screw 1506 and into a screw fitting 1618 that is threaded to receive the threads of the tightening screw 1506. The screw fitting 1618, contained within a moveable arm flange 1608, moves the adjustable arm 1604 toward the stationary arm 1602 as the tightening screw 1506 is tightened.

The support arm hinge 1514 includes a hinge attachment fitting 1614 that fits between the blades of a fork fitting 1612. The hinge attachment fitting 1614 is joined to the fork fitting 1612 by a hinge pin 1616 inserted through a series of aligned holes through the fork fitting 1612 and the hinge attachment fitting 1614. Any hinge mechanism known in the art may be used at any location along the support arm, so long as the support arm is capable of swinging away from the device 100 and cystoscope 106 when the support arm 1502 is detached from the device 100.

FIG. 17 is a cross-section of the support arm receptacle 1508 and support arm attachment fitting 1510. The support arm attachment fitting 1510 slides into the support arm receptacle 1508 and is held in the support arm receptacle 1508 by the fastening of the quick-release lever 1512.

Referring to FIG. 18, the support arm receptacle 1508 may have a square-shaped cross-sectional shape that fits into the square-shaped depression in the support arm attachment fitting 1510. Any cross-sectional shape may be used, so long as the rotation or other movement of the support arm attachment fitting 1510 relative to the support arm receptacle 1508 is minimized when the support arm 1502 is attached to the device 100.

The support arm 1502 may be constructed from any suitable rigid material possessing sufficient strength to support the device 100 during rotation of the laser fiber 104. In addition, the support arm material should be capable of withstanding the conditions of sterilization without distorting in shape or weakening in strength. Non-limiting suitable materials to be used for the support arm 1502 include high-temperature polymers, and metals such as stainless steel, aluminum, and titanium.

Figure 19:
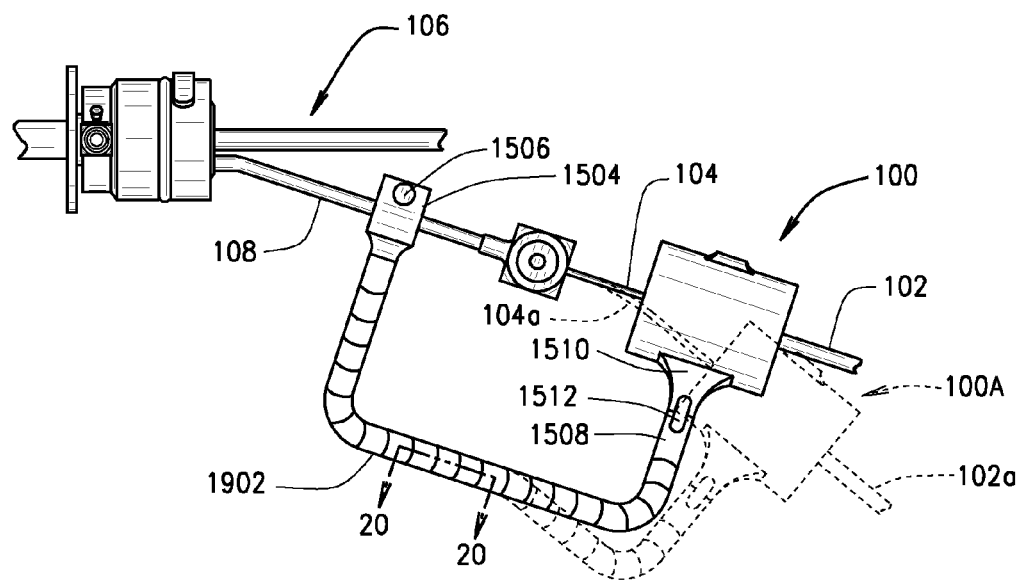
FIG. 19 is a side view of a laser surgery device attached to a cystoscope and mounted on a flexible support arm.

Referring to FIG. 19, a flexible support arm 1902 may be used to attach the device 100 to the cystoscope 106. The flexible support arm 1902 is designed to flex when pushed or twisted by the surgeon in order to adjust the position of the device 100 relative to the cystoscope 106 during the operation of the device 100. However, the flexible support arm 1902 should be suitably rigid in the absence of adjustments by the surgeon to allow hands-off operation of the device 100. In addition, the flexible support arm 1902 is designed to bend to away from the device 100 and cystoscope 106 when the device 100 is detached from the flexible support arm 1902.

Figure 20:
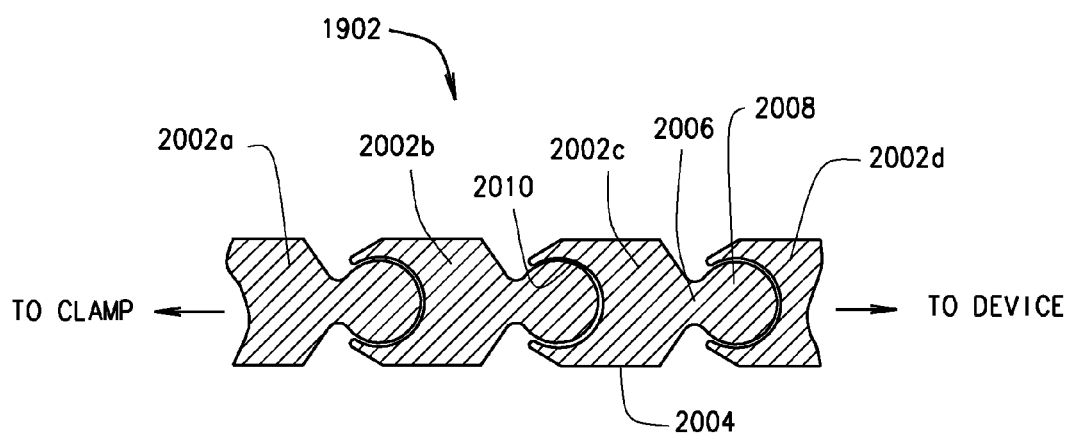
FIG. 20 is a cross-sectional view of a series of support arm links of a flexible attachment arm.

The flexible support arm 1902, as shown in cross-section in FIG. 20, may include a series of support arm links 2002A-D that are mechanically linked together in a sequential series. Each link 2002 includes a neck 2006 that connects to a spherical ball 2008 at one end of the link 2002. Within each link 2002, the neck 2006 and spherical ball 2008 are attached to a link body 2004. The opposite end of the link 2002 is formed into a cup-shaped socket fitting 2010 that is contoured to receive a ball 2008 from another link 2002. For example, the ball 2008 of link 2002a fits into the socket fitting 2010 of link 2002b, and the ball 2008 of link 2002b fits into the socket fitting 2010 of link 2002c, and so on. The ball 2008 and adjacent socket fitting 2010 form a ball-and-socket joint capable of rotating in any arbitrary direction in response to forces applied by the surgeon. However, the interface between each ball 2008 and its adjacent socket fitting 2010 should possess static friction forces that are sufficiently strong to hold the device 100 in place during rotation of the laser fiber 104.

Any material possessing sufficient material strength and static friction characteristics may be used in the construction of the flexible support arm. In addition, the material of the support arm should be capable of withstanding the conditions of sterilization without degrading. Non-limiting examples of suitable materials for the flexible support arm include high-temperature polymers, and metals such as stainless steel, aluminum, and titanium.

Referring to FIGS. 21 and 22, the motor used to rotate the interior cylinder 314 may be integrated into the structures of the device 100B. As shown previously, the device 100B may include an inner cylinder 314 that rotates within the interior surface 710 of the outer case 208 on a plurality of bearings 714 situated between two or more inner bearing channels 708 and corresponding outer bearing channels 712. The inner cylinder 314 typically has a larger outer diameter near the entrance 214 to accommodate the control knob lumen 204, and contracts to a smaller outer diameter in the region containing the laser fiber lumen 605. An inner compartment 718 is defined between the interior surface 710 of the outer case 208 and the outer surface 706 of the inner cylinder 314.

The device 100B also includes a nonferrous gear body 2102 attached to the outer surface 706 of the inner cylinder 314 such that the axis of rotation of the nonferrous gear body 2102 is coincident with the longitudinal axis of the inner cylinder 314. A plurality of ferrous gear teeth 2104 are attached to the outer surface of the nonferrous gear body 2102 in a circumferential pattern. Two or more electromagnets 2106A-D are attached to the interior surface 710 of the outer case 208 in alignment with the plurality of ferrous gear teeth 2104 and distributed around the circumference of the interior surface 710.

The plurality of ferrous gear teeth 2104 and the two or more electromagnets 2106A-D together function as a stepper motor. When one of the electromagnets 2106A is activated, the ferrous gear teeth 2104 in the vicinity of the activated electromagnet 2106A are attracted by the magnetic force generated by the activated electromagnet 2106A, causing a rotation of the inner cylinder 314. As each successive electromagnet 2106B-D is activated, all other electromagnets 2106 are inactivated, and the inner cylinder 314 is further rotated by the magnetic attraction between the ferrous gear teeth 2104 and the activated electromagnet 2106B-D.

The rotation speed, rotation direction, and sweep angle may all be determined by the activation sequence and timing of the electromagnets 2106A-D. The activation sequence and timing of the electromagnets 2106A-D may be controlled by the motor speed control circuit 732 and the motor sweep control circuit 734 (not shown). The period of time that each electromagnet 2106A-D is activated, and the total time taken to activate all electromagnets 2106A-D in the activation cycle may be used to control the rotation speed of the inner cylinder 314. The simultaneous activation or inactivation of all electromagnets 2106A-D may be used to stop the rotation of the inner cylinder 314. The sequential order in which each of the electromagnets 2106A-D is individually activated may be used to specify the direction of rotation of the inner cylinder 314.

For example, in order to achieve a clockwise rotation of the inner cylinder 314, the electromagnets may be activated in a repeating clockwise pattern such as electromagnetic 2106A, followed by electromagnetic 2106C, electromagnet 2106B, electromagnet 2106D, and then electromagnet 2106A to repeat the activation cycle. Similarly, the electromagnets may be activated in a counterclockwise pattern in order to reverse the direction of rotation of the inner cylinder 314.

IV. Installation of Laser Fiber into Device

In various configurations, the laser fiber 104 may be installed in the device 100 by sliding the laser fiber 104 through the entrance 214, as shown in FIG. 2. As shown in FIGS. 10-12, the device 100A may optionally open in a clamshell manner such that the laser fiber 104 (not shown) may be placed directly inside the laser fiber lumen 605 (not shown); the laser fiber 104 may then be secured by closing the device 100A using a latch 1102.

A. Slide Laser Fiber into Device

Referring to FIG. 2, the laser fiber 104 is inserted into the control knob lumen 204 at the entrance 214 of the device 100. As the laser fiber 104 is inserted, it passes through a laser fiber lumen 605 (not shown) that connects to the control knob lumen 204 and opens to the device exit 216. As the laser fiber 104 is pushed further through the device 100, the insertion face 228 of the control knob 202 is inserted into the control knob lumen 204.

The device 100 may include a contoured inner cylinder 206 that includes a plurality of ridges 222 separated by furrows 224. Each ridge 222 of the contoured inner cylinder 206 is contoured to be opposite in shape to each depression 218 of the control knob 202. Each furrow 224 of the contoured inner cylinder 206 is contoured to be opposite in shape to each knurl 220 of the control knob 202. As a result, the inner surface 702 (not shown) of the contoured inner cylinder 206 engages cooperatively with the control knob 202 as the control knob 202 is inserted into the contoured inner cylinder 206. The control knob 202 may be force-fit into the device 100 and held in place by frictional forces.

Alternatively, the control knob 202 may be held in place by a securing plug 300, as shown in FIG. 3A. The securing plug 300 may include a cylindrical plug body 302 contoured to fit within the control knob lumen 204 behind the control knob 202. The securing plug 300 may further include a plug notch 304 extending from the central axis radially downward through the lower edge of the plug body 302 for the entire length of the plug body 302. The securing plug 300 may also include an elongated insertion arm 308 attached to the removal end 312 of the securing plug 300. The insertion arm 308 may be mechanically engaged to the ratchet catch 306 such that the ratchet catch 306 is reversibly retracted by applying a lateral inward force to the insertion arm 308.

The plug notch 304 of the securing plug 300 may be slipped over the shielded laser fiber 102, as shown in FIG. 3A. The securing plug 300 may be slipped along the shielded laser fiber 102 toward the control knob lumen 204. The insertion arm 308 may then be used to push the securing plug 300 further into the control knob lumen 204 until the insertion end 310 of the securing plug 300 butts up against the removal face 226 of the control knob 202, thereby holding the laser fiber 104 and control knob 202 in place. The securing plug 300 is shown fully inserted into the control knob lumen 204 in FIG. 3B.

Figure 4:
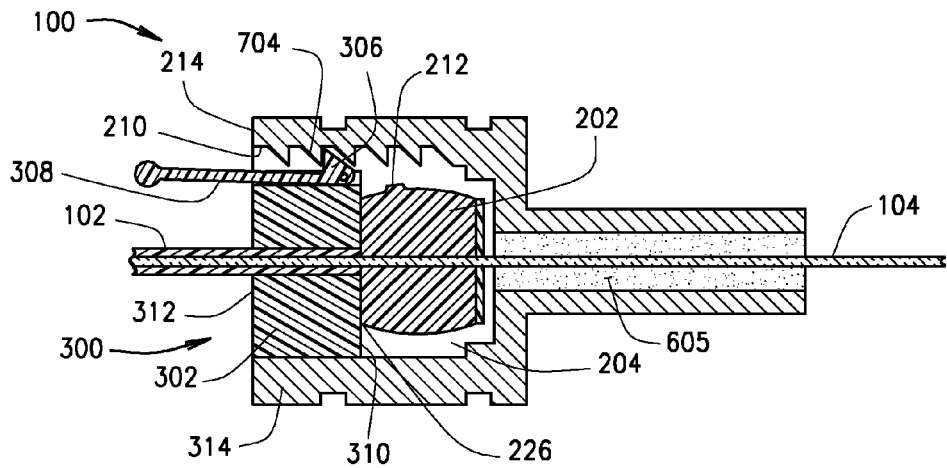
FIG. 4 is a longitudinal cross-sectional view of a control knob and a retaining plug inserted in an inner cylinder of a laser surgery device.

The securing plug 300 may further include a ratchet catch 306 designed to mesh with at least one ratchet tooth 704 on the upper part of the notch 210 in the inner cylinder 314, as shown in FIG. 4. After the control knob 202 is inserted into the control knob lumen 204, the securing plug 300 is inserted into the control knob lumen 204 such that the ratchet catch 306 engages with at least one ratchet tooth 704. As the securing plug 300 advances into the control knob lumen 204, the ratchet catch 306 deflects downward as it passes each ratchet tooth 704 and returns to an undeflected position between adjacent ratchet teeth 704. The securing plug 300 is advanced into the control knob lumen 204 until the insertion end 310 is pressed against the removal face 226 of the control knob 202. The control knob 202 is immovably held in place by the pressure of the insertion end 310 of the securing plug 300 against the removal face 226 of the control knob 202.

Once installed, the securing plug 300 is held in place by the ratchet catch 306, which is mechanically engaged with one of the ratchet teeth 704. To remove the securing plug 300, a lateral force may be applied to the insertion arm 308, causing the retraction of the ratchet catch 306 into the plug body 302. The securing plug 300 may then be pulled out of the control knob lumen 204.

Alternatively, the plug body 302 may be contoured such that the securing plug 300 may be inserted and force-fit into the control knob lumen 204 and held in place by frictional forces. The securing plug 300 may optionally be threaded on its outer surface in order to twist into the control knob lumen 204 and the inner surface of the control knob lumen 204 may be similarly threaded to receive the plug body 302. The securing plug 300 may be held in place using magnets incorporated into the plug body 302 and the inner cylinder 314, using a clip mounted on the shielded laser fiber 102 between the plug body 302 and the entrance 214, a clip attached to the outer case 208, by retaining pins extending from the plug body 302 into the inner cylinder 314, or by retaining pins extending from the inner cylinder 314 into the plug body 302.

B. Place Laser Fiber into Device with Clamshell Outer Casing

The device 100A may optionally open in a clam-shell fashion, as previously described and illustrated in FIG. 10 and FIG. 11. The device 100A may be opened to expose the lower member 1010, as illustrated in FIG. 12. After the device 100A is opened, the laser fiber 104 is placed into the laser fiber lumen 608 and the control knob 202 is placed in the control knob lumen 204. The control knob lumen 204 may be contoured to closely fit the external shape of the control knob 202. The upper casing 1004 (not shown) is then closed over the lower casing 1006 and secured by fastening the latch 1102 (not shown). The tension of the fastened latch 1102 clamps the control knob 202 and laser fiber 104 securely inside the control knob lumen 204 and the laser fiber lumen 608 respectively.

Alternatively, the control knob lumen 204 may be lined with a compressible material (not shown) to enhance the fit of the control knob 202 within the control knob lumen 204. This compressible material may be attached to the inner surface 702 within the control knob lumen 204. Any suitable compressible material may be used including but not limited to natural rubber, synthetic polyisoprene, butyl rubber, polybutadiene, styrene-butadiene rubber, nitrile rubber, chloroprene rubber, polychloroprene, ethylene propylene rubber, ethylene propylene diene rubber, epichlorohydrin rubber, polyacrylic rubber, silicone rubber, fluorosilicone rubber, polyether block amides, chlorosulfonated polyethylene, ethylene-vinyl acetate, and combinations thereof.

V. Method of Using Device

The device 100 may be used to perform a laser surgical procedure. The method of performing a surgical laser procedure includes providing a surgical laser fiber 104 protruding from a control knob 202, sliding the laser fiber 104 through the laser fiber lumen 605 as described above, and inserting the securing plug 300 behind the control knob 202 to securely fasten the laser fiber 104 and control knob 202 inside the device 100. This method further includes threading the laser fiber 104 through the working channel 108 of the cystoscope 106 until the laser fiber 104 is in the proximity of the surgical site. Once the laser fiber 104 is in place in the surgical site, the rotation speed control 602 and rotation sweep control 604 are activated, resulting in the activation of the motor speed control circuit 732 and motor sweep control circuit 734, respectively. The motor control circuitry 730 activates the power unit 726, which in turn rotates the driveshaft 724. The rotation of the driveshaft 724 is transmitted to the inner cylinder 314 via the transmission gear 720. The rotation of the inner cylinder 314 imparts a corresponding rotation to the laser fiber 104, which is secured within the inner cylinder 314. The rotational motion of the laser fiber 104 may include a repeated pattern described above. This method further includes activating the laser source that is connected to the laser fiber 104, resulting in the release of laser energy into the surgical site.

The rotation speed and/or the sweep angle associated with the rotational motion of the laser fiber 104 may be held at essentially constant values for the duration of the surgical procedure. Alternatively, the rotation speed and/or sweep angle may be increased or decreased independently during the duration of the surgical procedure by manipulating the rotation speed control 602 and rotation sweep control 604, respectively.

In an alternative method of performing a surgical laser procedure, the laser fiber 104 and control knob 202 may be placed inside of the device 100 by opening the device 100 in a clamshell-like manner and placing the laser fiber 104 and control knob 202 into the laser fiber lumen 605 and control knob lumen 204 and closing the device 100, as described above. This method performing a surgical laser procedure then proceeds by activating the rotation speed control 602, rotation sweep control 604, and laser source as described above.

VI. Alternative Aspects of the Device

A. Alternative Motions of Laser Fiber

The device 100 may impart alternative motions to the laser fiber 104 in addition to the rotational movements described above during operation of the device 100. The device 100 may impart a displacement along the longitudinal axis of the laser fiber 104 corresponding to an insertion or withdrawal motion of the laser fiber 104 from the surgical site. The displacement along the longitudinal axis may occur in a forward direction and then a reverse direction in a repeating cycle, corresponding to a cyclic insertion and withdrawal motion. Alternatively, the displacement along the longitudinal axis may occur in a the insertion direction only, or in the withdrawal direction only, with no cyclic longitudinal direction change. The speed of the longitudinal motion, and the displacement distance relative to a reference displacement may be independently varied during the rotation of the laser fiber 104 by the device 100.

The longitudinal and rotational movements of the laser fiber 104 may be accomplished simultaneously, or the longitudinal movements may be accomplished independently of the rotational movements. The longitudinal movements may further be implemented as a direct function of the rotational movements. The functional dependence of the longitudinal movements upon the rotational movements may be determined by the motor speed control circuit 732, motor sweep control circuit 734, or any combination thereof. A separate switch may be included in the device 100 to control the longitudinal motion of the laser fiber 104, or the longitudinal control function may be integrated into one or more switches that also control the rotational movement of the laser fiber 104.

B. Alternative Control Schemes of Laser Fiber Movement

The device 100 may implement any one or more of at least several control schemes to control the movement of the laser fiber 104 by the device 100. The rotation speed, sweep angle, longitudinal displacement distance and longitudinal displacement speed may be controlled independently using the corresponding controls. Alternatively, the rotation speed, sweep angle, longitudinal displacement speed, and longitudinal displacement distance may be controlled in a coordinated manner using a feedback control scheme in which any one or more of the states of the laser fiber motion including but not limited to rotation speed, sweep angle, longitudinal displacement speed, and longitudinal displacement distance are measured and communicated to a control system that may automatically adjust any one or more of the states of the laser fiber motion using one or more previously stored functions of any one or more of the states of the laser fiber motion. Any one or more of the states of the laser fiber motion may be adjusted as a function of other measured feedback quantities including but not limited to the cavitation of the fluid in the surgical site, the temperature of the fluid in the surgical site, the location of the laser fiber tip 124 within the surgical site, the temperature of the laser tip 124, the color of tissues in the surgical site, and the laser power setting of the laser source.

In one illustrative example, the device 100 may include a control system scheme in which the rotation speed is adjusted as a function of the sweep angle, in order to maintain a constant rotation period, defined herein as the time taken by the laser fiber 104 to rotate from its most clockwise position to its most counterclockwise position and back to its starting position. In this example, the control system would slow down the rotation speed of the laser fiber 104 if the surgeon commanded a narrower sweep angle, so that the time taken by the laser fiber 104 to sweep through one cycle at the narrower sweep angle was the same as the time taken to sweep through one cycle at the previous wider sweep angle.

C. Recording and Storage of Laser Fiber Movements

The device 100 may optionally include computer readable media to store the laser fiber movements accomplished by the device 100 for review after completion of the surgical procedure. The computer readable media may include volatile media, nonvolatile media, removable media, non-removable media, and/or other media that can be accessed by a general purpose or special purpose computing device. For example, computer readable media may include computer storage media and communication media. Computer storage media further may include volatile, nonvolatile, removable, and/or non-removable media implemented in a method or technology for storage of information, such as computer readable instructions, data structures, program modules, and/or other data. Communication media may, for example, embody computer readable instructions, data structures, program modules, algorithms, and/or other data, including as or in a modulated data signal. The communication media may include an information delivery system. The communication media may include wired and/or wireless connections and technologies and may be used to transmit and/or receive wired or wireless communications. Combinations and/or sub-combinations of the systems, components, modules, and methods and processes described herein may be made.

The computer readable media may record any data signal generated by the device 100 that may be used to reconstruct the laser fiber movements accomplished by the device 100 during a surgical procedure. Non-limiting data signals that may be recorded on the computer readable media include electrical signals such as voltages and currents generated by any of the electrical components of the device 100 including but not limited to the motor control system, power supply, and motor.

Alternatively, the computer readable media may record signals generated by sensors included in the device 100 to monitor the laser fiber movements. Non-limiting examples of sensors suitable for incorporation into the device 100 include potentiometers, accelerometers, linear variable differential transformers (LVDTs), capacitive transducers, proximity sensors, rotary encoders, piezo-electric transducers, and photodiode arrays.

Those skilled in the art will appreciate that variations from the specific embodiments disclosed above are contemplated by the invention. The invention should not be restricted to the above embodiments, but should be measured by the following claims.

What is claimed is:

1. A laser surgery device to detachably receive an endoscopic surgical laser comprising a laser fiber, a control knob, and a shielded laser fiber connecting the laser fiber to a laser source, the device comprising:
 a. an outer case comprising an exterior surface, an interior surface, an upper casing, and a lower casing, wherein:
  i. the upper casing and the lower casing are hingeably connected along a hinge line by two or more hinges attached to the exterior surface;
  ii. the upper casing and lower casing are reversibly secured at a diametrically opposite line of intersection by at least one latch attached to the exterior surface; and,
  iii. the interior surface defines a main lumen extending along a longitudinal axis of the outer case;
 b. an inner cylinder situated within the main lumen and rotatably connected to the interior surface of the outer case such that an axis of rotation of the inner cylinder coincides with the longitudinal axis of the outer case, and the inner cylinder rotates within the outer case, wherein:
  i. the inner cylinder comprises an inner surface, an outer surface, an upper member, and a lower member, wherein the upper member is attached to the upper casing and the lower member is attached to the lower casing when the outer cylinder is in an open position; and,
  ii. the inner surface defines the walls of a laser lumen fitted to the external shape of the laser fiber, control knob, and shielded laser fiber, wherein:
   1. the shielded laser fiber, control knob, and laser fiber are placed within the inner cylinder such that the laser fiber protrudes from one end of the laser lumen and the shielded laser fiber protrudes from the opposite end of the laser fiber lumen; and,
   2. the upper member and lower member reversibly clamp the laser fiber within the laser lumen of the inner cylinder when the outer case is latched in a closed position to detachably receive and hold the laser fiber;
 c. an electrical motor comprising a driveshaft protruding from a motor unit wherein the motor unit is attached to the interior surface of the outer case;
 d. a power source electrically connected to the motor;
 e. a drive gear attached to the end of the driveshaft opposite to the motor unit;
 f. a transmission gear attached to the outer surface of the inner cylinder, wherein the transmission gear meshes with the drive gear;
 g. a motor sweep control circuit electrically connected to the electrical motor; and,
 h. a motor speed control circuit electrically connected to the electrical motor; and,
wherein the device rotates the laser fiber by the rotation of the inner cylinder.

2. The device of claim 1, wherein the device rotates the laser fiber in an user-specified repeating pattern comprising a clockwise rotation followed by a counterclockwise rotation through a sweep angle ranging from 90° clockwise to 90° counterclockwise relative to a downward vertical reference plane.

3. The device of claim 2, wherein the upper casing and the lower casing comprise half-cylinder shells.

4. The device of claim 1, wherein the upper member and the lower member comprise half-cylinder shells.

5. The device of claim 1, wherein the motor is integrated into the inner cylinder and the outer case.

6. The device of claim 1, wherein the rotational movement of the laser fiber is a user-specified repeating pattern.

7. The device of claim 1, wherein the laser surgery device attaches to a surgical device.

8. The device of claim 7, wherein the surgical device is a cystoscope.

9. The device of claim 1, wherein the laser source ablates, vaporizes, or cauterizes prostate tissue.

10. The device of claim 1, wherein a laser fiber tip of the laser fiber protrudes from the laser fiber lumen at a device exit.

11. The device of claim 1, wherein the device rotates the laser fiber at an essentially constant rotational speed ranging from 5°/second to 360°/second.

12. The device of claim 1, wherein the transmission gears rotates the inner cylinder.

13. The device of claim 1, wherein the inner cylinder holds and rotates the laser fiber.

14. The device of claim 1, wherein the inner cylinder rotates within the outer case and rotates the laser fiber.

15. The device of claim 1, wherein the laser lumen comprises a control knob lumen and a laser fiber lumen, and the control knob lumen has a larger diameter than the laser fiber lumen.

* * * * *